(12) United States Patent
Meretei

(10) Patent No.: US 7,458,930 B2
(45) Date of Patent: Dec. 2, 2008

(54) ARTIFICIAL SPHINCTER WITH VARIABLE VISCOSITY FLUID-FILLED COLLAR

(75) Inventor: Attila Meretei, Fremont, CA (US)

(73) Assignee: Nitinol Development Corporation, Fremont, CA (US)

( * ) Notice: Subject to any disclaimer, the term of this patent is extended or adjusted under 35 U.S.C. 154(b) by 344 days.

(21) Appl. No.: 11/025,235

(22) Filed: Dec. 29, 2004

(65) Prior Publication Data

US 2006/0142636 A1 Jun. 29, 2006

(51) Int. Cl.
*A61F 2/02* (2006.01)
(52) U.S. Cl. .................................................... 600/30
(58) Field of Classification Search ............. 600/29–32, 600/38–41; 623/11.11, 14.13
See application file for complete search history.

(56) References Cited

U.S. PATENT DOCUMENTS

| | | | | |
|---|---|---|---|---|
| 4,408,597 A | * | 10/1983 | Tenney, Jr. .................. | 600/31 |
| 4,664,100 A | * | 5/1987 | Rudloff ........................ | 600/40 |
| 5,509,888 A | | 4/1996 | Miller et al. .................. | 600/29 |
| 5,624,727 A | * | 4/1997 | Stoy ............................ | 428/76 |
| 5,975,081 A | * | 11/1999 | Hood et al. .................. | 128/845 |
| 6,638,208 B1 | | 10/2003 | Natarajan et al. ............. | 600/30 |
| 2003/0144575 A1 | | 7/2003 | Forsell ........................ | 600/29 |
| 2004/0172087 A1 | | 9/2004 | Forsell ........................ | 607/40 |

OTHER PUBLICATIONS

European Search Report EP 05257902.6 dated Apr. 19, 2006.

\* cited by examiner

*Primary Examiner*—Samuel G Gilbert

(57) ABSTRACT

Systems and methods for supplementing control of an anatomical sphincter. A collar containing variable viscosity fluid surrounds a portion of an anatomical conduit. The flow of bodily fluids through the anatomical conduit occurs according to the viscosity level of the variable viscosity fluid. Electro-rheologic fluid in the collar liquefies in the absence of an electrical potential difference to render the collar pliable, permitting the anatomical conduit to expand and fluid to flow through the anatomical conduit. Electro-rheologic fluid in the collar solidifies in the presence of an electrical potential difference to render the collar firm, restricting the anatomical conduit from expanding and restricting fluid from passing through the anatomical conduit. A control unit, or battery, operable in response to sensed pressure data or according to an external control unit manipulated by a patient, determines when an electrical potential difference is generated to change the state of the electro-rheologic fluid in the collar. Other fluids may be utilized in the collar, such as magneto-rheologic fluids.

16 Claims, 7 Drawing Sheets

FIG. 1 PRIOR ART
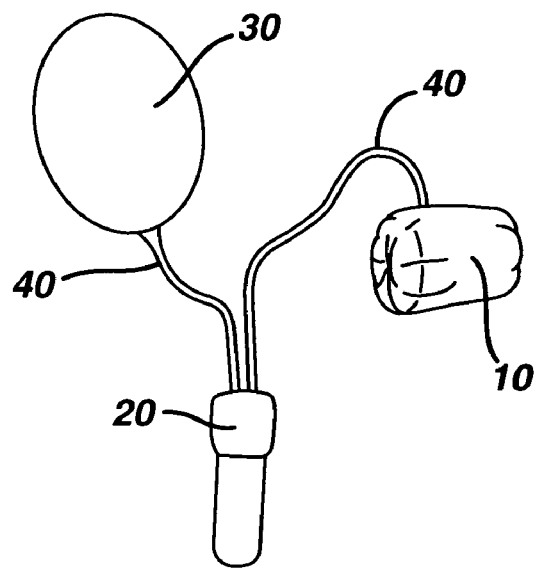
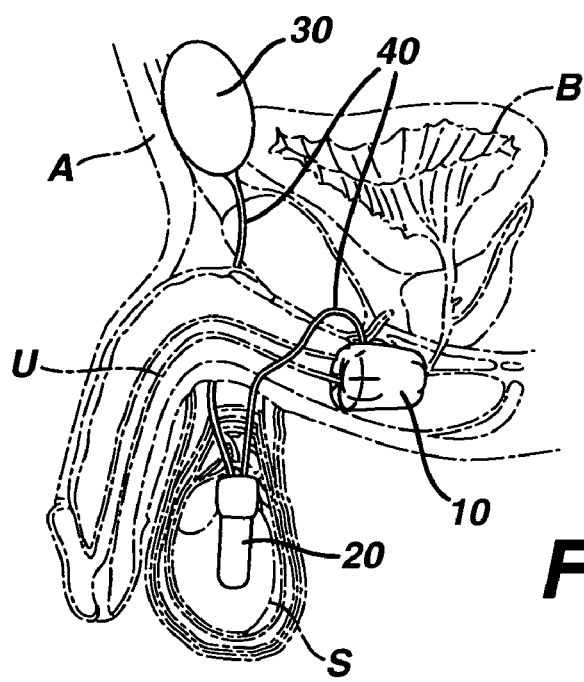
FIG. 2 PRIOR ART

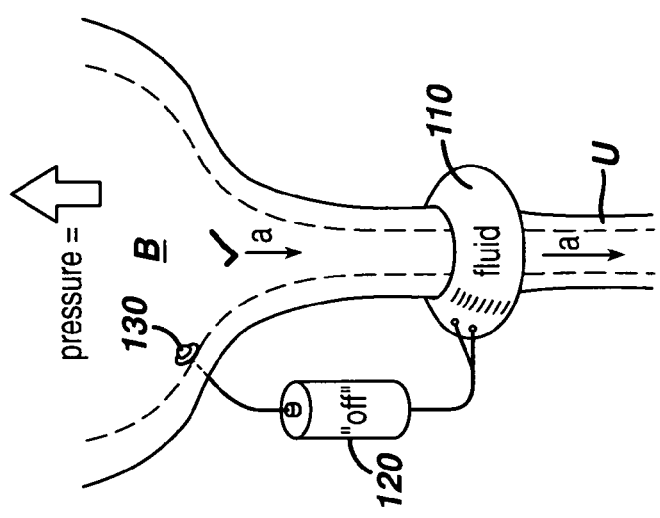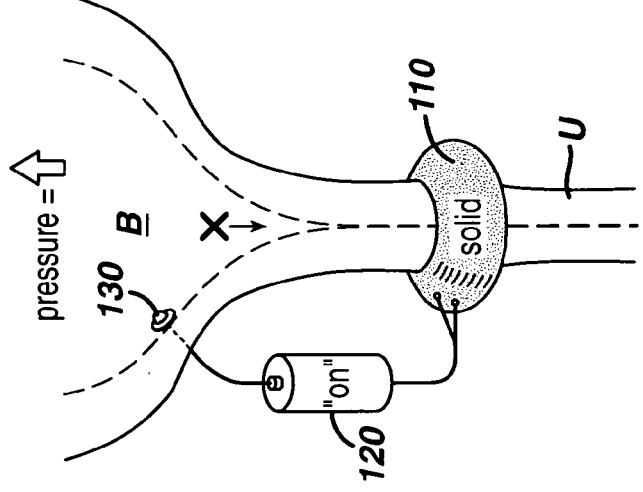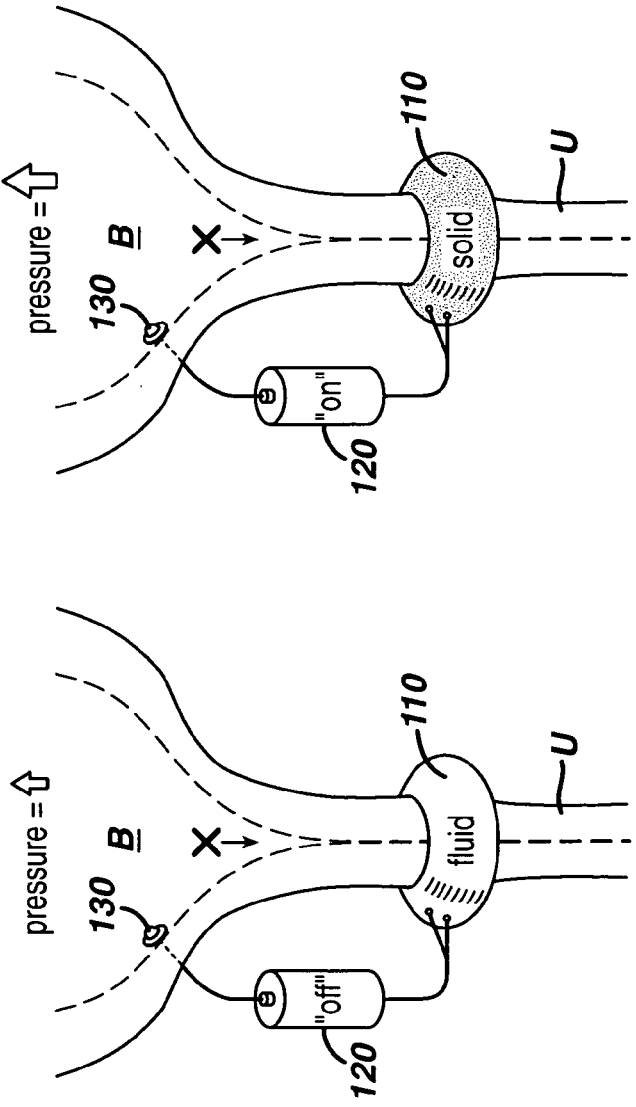

ARTIFICIAL SPHINCTER WITH VARIABLE VISCOSITY FLUID-FILLED COLLAR

BACKGROUND OF THE INVENTION

1. Field of the Invention

The invention generally relates to systems and methods for artificially supplementing the function of a sphincter muscle in a patient. More specifically, the invention relates to systems and methods for supplementing the function of the sphincter muscle by changing the viscosity state of fluid within a collar that encircles a portion of an anatomical conduit controlled by the sphincter muscle.

2. Discussion of the Related Art

Control of urinary continence depends on the function of the sphincter muscle straddling the urethra of a person. Ideally, the sphincter muscle squeezes the urethra to stop the flow of urine from the bladder and relaxes to open the passageway of the urethra when elimination of urine from the bladder through the urethra is desired. Over time, the function of the anatomical sphincter muscles can become damaged, weakened, or otherwise impaired such that the sphincter muscle is partially or completely unable to squeeze the urethra sufficiently to prevent unintended flowing of fluids from the bladder. As a result, incontinence may occur. Artificial sphincters have been developed to treat incontinence in persons having weakened or otherwise impaired sphincter muscles.

FIG. 1 shows an exemplary conventional artificial sphincter control system. The system shown in FIG. 1 comprises a cuff 10, a pump 20, a balloon reservoir 30 and tubing 40 connecting the various components to one another. Such artificial sphincters are typically surgically implanted in a patient through incisions in the lower abdomen and labia for females, and in the abdomen, scrotum, and between the scrotum and anus for males. FIG. 2 illustrates such a conventional device implanted in a male.

As shown in FIG. 2, the cuff 10 surrounds a portion of the urethra U, the pump 10 is placed within the scrotum S, and the balloon reservoir 30 is placed in the lower abdomen A. Tubes 40 connect the various components. In practice, the conventional cuff 10 is inflated using fluid from the balloon reservoir 30. The inflated cuff 10 squeezes that portion of the urethra U that is surrounded with the cuff. The inflated cuff 10 squeezes the urethra closed and thus stops urine from flowing from the bladder B through the urethra.

The pump 20, placed within the scrotum S as shown in FIG. 2, controls the movement of fluid to and from the cuff 10 and the balloon reservoir 30. For example, manually pressing the pump 20 deflates the cuff 10 by displacing fluid from the cuff 10 to the balloon reservoir 30. When the cuff 10 is deflated, the urethra is opened and urine is able to pass there-through for elimination from the body. After a designated time period has passed, for example, 2-3 minutes, fluid automatically leaves the balloon reservoir 30 and returns to the cuff 10 to inflate the cuff 10 once again. As before, when the cuff 10 is fully inflated, the urethra is generally squeezed closed and urine does not pass there-through.

Although the systems and methods of known artificial sphincters, such as those described above, offer supplemental function to a compromised sphincter muscle, the placement of the pump in the labia or scrotum of an individual can interfere with other physical activities. Moreover, inadequate emptying of the bladder may occur if the cuff 10 becomes re-inflated too quickly, as might occur when the pump 10 is insufficiently depressed such that only small amounts of fluid are displaced from the cuff 10 to the balloon reservoir 30. Still further, the network of artificial conduits connecting the pump, the collar and the balloon reservoir of conventional systems is subject to infection and/or stoppages that can render the device unreliable. Such problems are often only remedied by additional surgeries.

In view of the above, a need exists for systems and methods that simplify and render more reliable the supplemental control of an anatomical sphincter muscle.

SUMMARY OF THE INVENTION

The systems and methods of the invention provide an artificial sphincter system for supplementing the function of an anatomical sphincter muscle of a patient. The artificial sphincter system comprises at least a collar surrounding a portion of an anatomical conduit, such as an urethra, and a variable viscosity fluid contained within the collar. When liquefied, the variable viscosity fluid renders the collar pliable permitting the anatomical conduit surrounded by the collar to expand freely and pass bodily fluids therethrough the anatomical conduit, as from a bladder. When solidified, the variable viscosity fluid renders the collar rigid thereby restricting the anatomical conduit from expanding and restricting bodily fluids from passing therethrough the anatomical conduit.

Changes in the state of the variable viscosity fluid thus determine whether the collar restricts or permits bodily fluids to pass through that portion of the anatomical conduit surrounded by the collar. Generally, the lower the viscosity level of the fluid in the collar the more pliable the collar is. The more pliable the collar is, the more easily bodily fluids are passed there-through that portion of the anatomical conduit surrounded by the collar.

Some embodiments of the systems and methods of the invention further provide an artificial sphincter system wherein the variable viscosity fluid in the collar is an electro-rheologic fluid. The electro-rheologic fluid is comprised of a suspension of dielectric particles that change state when exposed to an electric field. The electro-rheologic fluid tends to solidify when exposed to conditions such as an electrical potential difference, thus rendering the collar more rigid, which in turn restricts the anatomical conduit from expanding and thus restricts the flow of bodily fluids through that portion of the anatomical conduit surrounded by the collar. Conversely, in the absence of an electrical potential difference, the electro-rheologic fluid tends to be more liquified, thus rendering the collar more pliable, which in turn permits expansion of the anatomical conduit and thus permits bodily fluids to flow more easily through the anatomical conduit surrounded by the collar.

In some embodiments of the systems and methods of the invention provided with an electro-rheologic fluid, the invention further provides an implanted control unit, or battery, connected to the collar. An electrical potential difference generated by the implanted control unit, or battery, and communicated to the collar causes the electro-rheologic fluid to solidify. When the electrical potential difference is not generated and communicated to the collar, the electro-rheologic fluid tends to liquefy. The implanted control unit, or battery, generates the electrical potential difference in response to sensed pressure data from a sensor placed within the anatomical conduit or organ to be emptied through the anatomical conduit, or in response to operator input provided to an external control unit operable at will by the patient and that communicates with the implantable control unit, or battery.

Other embodiments of the systems and methods of the invention provided with an electro-rheological fluid omit the implantable control device, or battery, and instead extend the wire connected to the collar to a position located external to the patient's body. The wires connected to the collar communicate the electrical potential difference to the collar in similar manner based on pressure data sensed from a sensor placed within the anatomical conduit or organ to be emptied through the anatomical conduit, or in response to operator input provided to the external control unit.

Still other embodiments of the systems and methods of the invention provide an artificial sphincter system wherein the fluid in the collar is a magneto-rheologic fluid. The magneto-rheologic fluid tends to liquefy in the absence of a magnetic field, thus rendering the collar more pliable, and tends to solidify in the presence of a magnetic field, thus rendering the collar more rigid. The flow of bodily fluids through that portion of the anatomical conduit surrounded by the collar containing the magneto-rheologic fluid would be permitted or restricted accordingly.

In those embodiments of the systems and methods of the invention provided with a collar having magneto-rheologic fluid, a control unit comprises a magnetic field generator that generates conditions such as a magnetic field in response to sensed pressure data from the sensor placed within the anatomical conduit or organ to be emptied through the anatomical conduit, or in response to the external control unit operated by the patient. The absence or presence of the magnetic field alters the viscosity state of the magneto-rheologic fluid similarly to that described above with respect to the electro-rheologic fluid. The magnetic field generator may be implanted within the patient's body or may be outside the patient's body. Servicing the magnetic field generator may be easier, and fewer biocompatibility issues may arise, when the magnetic field generator is placed outside the body.

In the various embodiments of the systems and methods of the artificial sphincter system according to the invention, a pressure sensor is provided in the anatomical conduit or organ to be emptied through the anatomical conduit upstream of the collar. The sensor can be a wireless sensor that communicates with the implanted control unit, battery, or magnetic field generator as the case may be, or the sensor can be a wired sensor physically connected to the implanted control unit, battery, or magnetic field generator. Regulation of the collar and the state of the variable viscosity fluid contained therein by the generation of the electric or magnetic field, is thus determined by data sensed by the pressure sensor or by operation of the external control unit by the patient.

The various methods of supplementing control of an anatomical conduit surrounded in part by the collar containing variable viscosity fluid according to the invention comprise at least permitting bodily fluids to flow through the anatomical conduit by liquefying the variable viscosity fluid in the collar to permit expansion of the anatomical conduit, and restricting the flow of bodily fluids through the anatomical conduit by solidifying the variable viscosity fluid in the collar and restricting the anatomical conduit from expanding, which in turn restricts the flow of bodily fluids there-through. The collar may comprise a single chamber within which the variable viscosity fluid is contained, or may comprise a plurality of compartments within which the variable viscosity fluid is contained.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

FIG. 1 illustrates components of a conventional artificial sphincter system.

FIG. 2 illustrates the placement of the conventional artificial sphincter system of FIG. 1 about a male anatomy.

FIG. 6A-6C schematically illustrates various states of the variable viscosity fluid during deployment of the collar according to the invention.

DETAILED DESCRIPTION OF THE INVENTION

Figure 3:
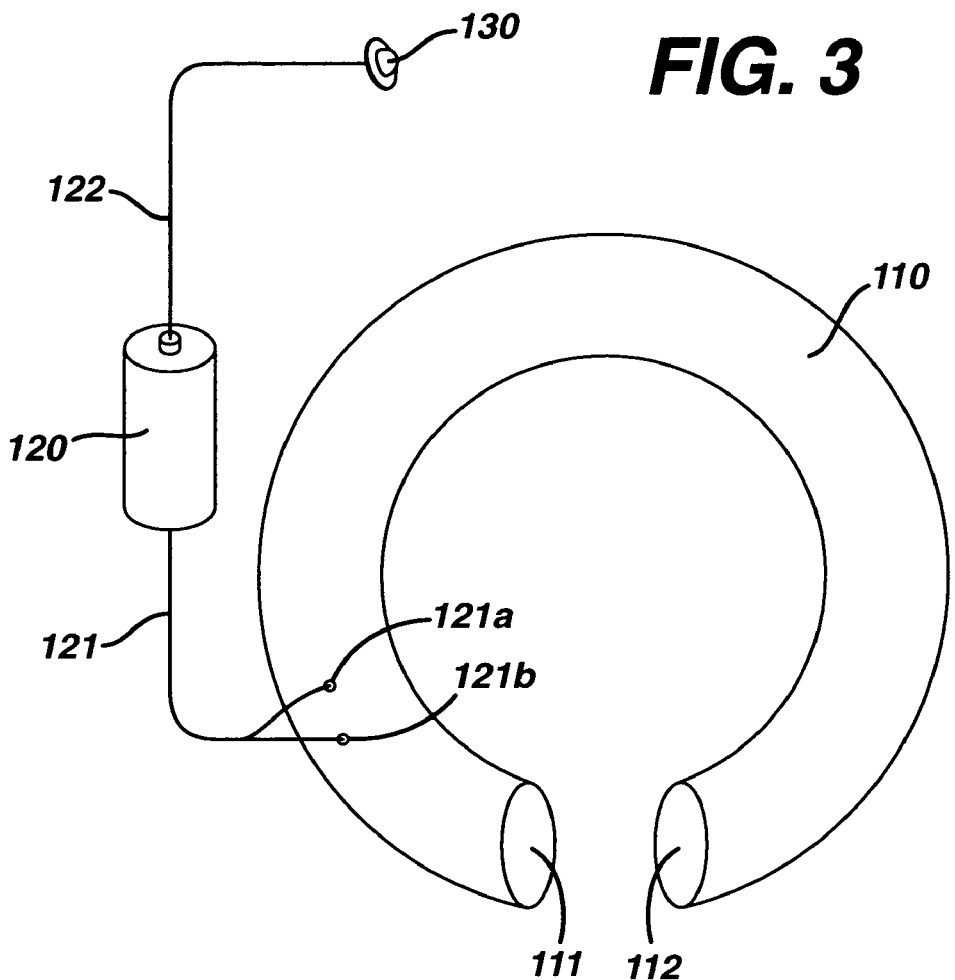
FIG. 3 illustrates one embodiment of an artificial sphincter system having an electro-rheologic fluid contained within the collar according to the invention.
Figure 5:
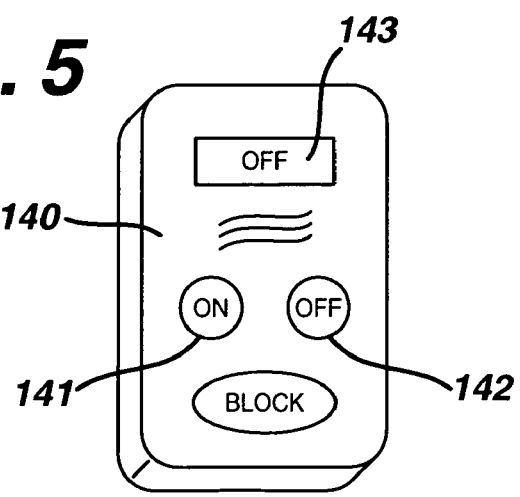
FIG. 5 illustrates an external control unit according to the invention.
Figure 4:
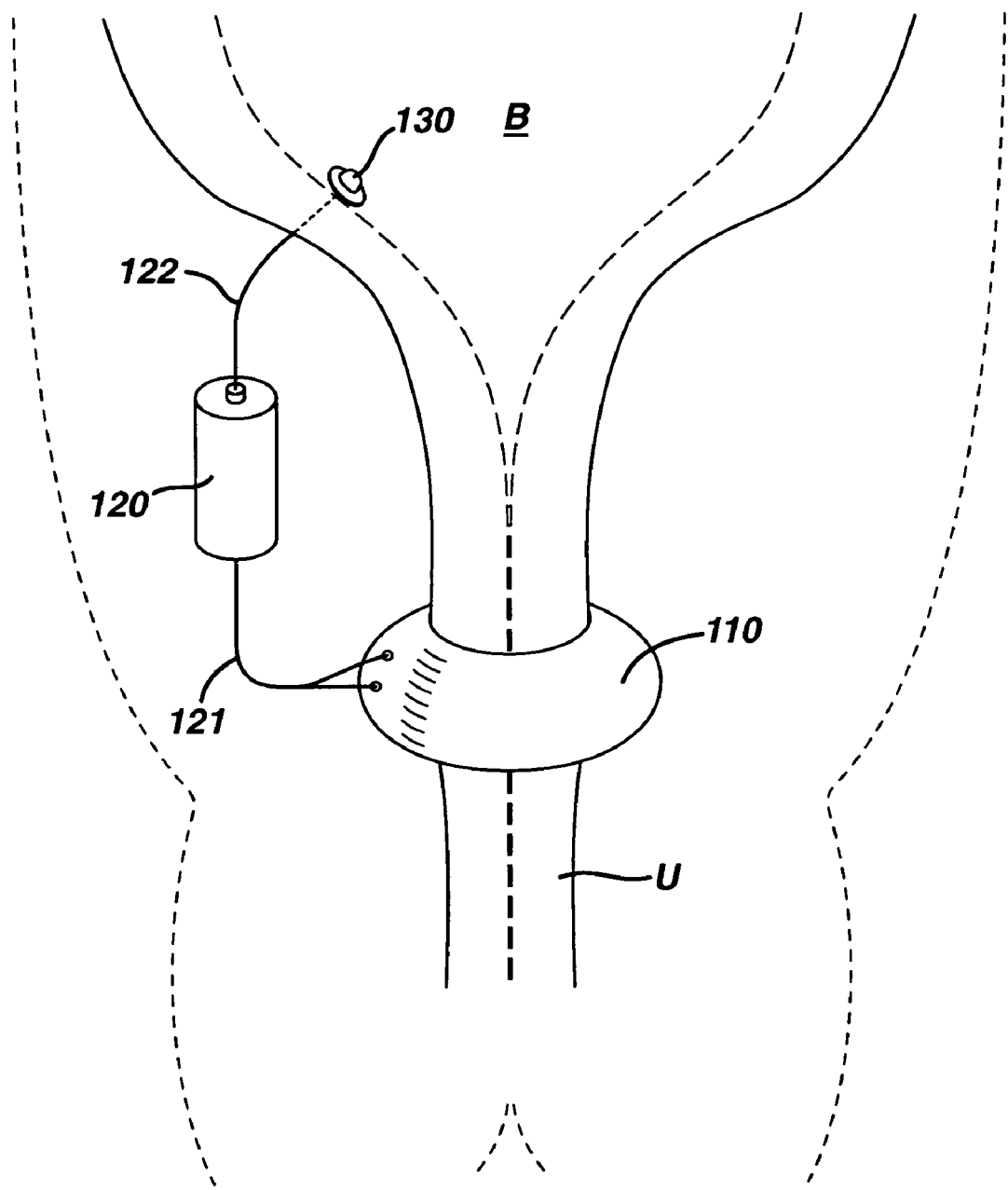
FIG. 4 illustrates the anatomical placement of the system of FIG. 3.

FIG. 3 illustrates various components of one embodiment of an artificial sphincter system according to the invention. As shown in FIG. 3, the artificial sphincter system is comprised of a collar 110 containing a variable viscosity fluid, an implantable control unit 120 connected to the collar, and a sensor 130 connected to the implantable control unit 120. The collar 110 surrounds an anatomical conduit, such as an urethra U (FIG. 4). The state of the variable viscosity fluid within the collar 110 determines the rigidity or pliability of the collar 110 and thus the expandibility of the anatomical conduit. FIG. 5 illustrates an external control unit 140 usable in combination with the various artificial sphincter systems and methods described herein.

Figure 8:
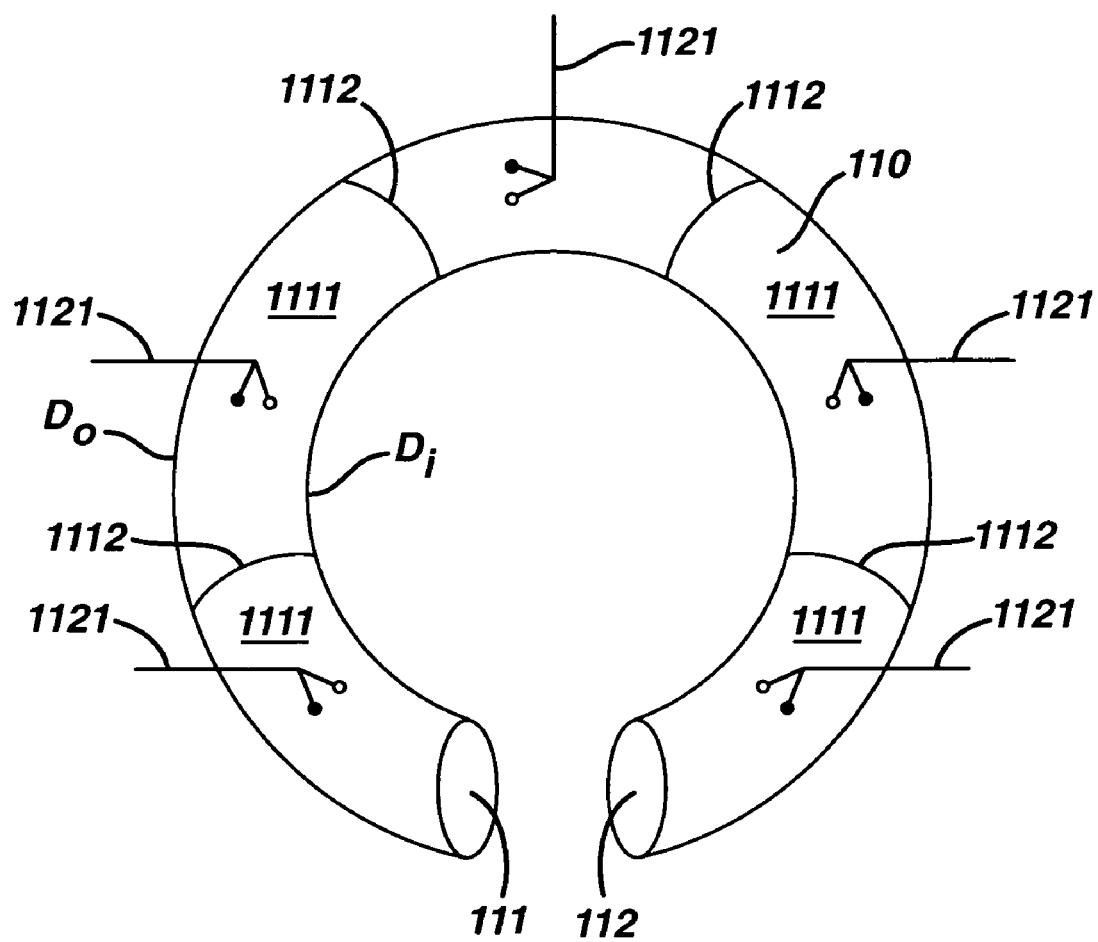
FIG. 8 illustrates an embodiment of a compartmentalized collar according to the invention.

Referring again to FIG. 3, the collar 110 is comprised generally of flexible, bio-compatible material as known in the art. Preferably, the collar 110 is biased in a circular, or semi-circular, configuration such that when placed about an anatomical conduit, such as an urethra U, the collar 110 will encircle an outer wall of the anatomical conduit. A variable viscosity fluid, such as, for example, an electro-rheologic fluid or a magneto-rheologic fluid, is contained within the collar 110. Closed ends 111, 112 of the collar 110 help to retain the variable viscosity fluid within the collar 110. The closed ends 111, 112 may be separated slightly from each other prior to placement of the collar 110 about the anatomical conduit in order to place the collar 110 around the desired anatomical conduit. Once in place around the anatomical conduit, the closed ends 111, 112 of the collar 110 are aligned with and secured to one another using a securing device (not shown), such as a clamp, buttons, snaps, sutures, or other device known in the art. FIG. 8 illustrates another collar 1110 having compartments 1111 for containing the variable viscosity fluid therein, as described in more detail below with respect to FIG. 8.

Referring again to FIG. 3, the implantable control unit 120, which may comprise a battery, may be connected to the collar 110 by a wire 121, having two leads 121a, 121b connected to the collar 110. An electrical potential difference can thus be applied and communicated to the collar 110 through the two leads 121a, 121b. The length of wire 121 can vary to accommodate placement of the implantable control unit 120, or battery, at different locations within the body of the patient. Typically, the implantable control unit 120, or battery, is placed within the lower abdominal regions of the patient, although the artisan will readily appreciate that placement of the implantable control unit 120, or battery, at other locations within the patient's body is within the scope of the invention by varying the length of the wire 121.

The implantable control unit 120, or battery, may also be connected to the sensor 130 by a wire 122. The sensor 130 is typically located upstream of the collar 110 within the anatomical conduit, or within an organ that is to be emptied through the anatomical conduit. The length of wire 122 may be varied to accommodate the placement of the implantable control unit 120, or battery, and the placement of the sensor 130 as desired. Alternatively, the wire 122 may be omitted and the sensor 130 and implantable control unit 120, or battery, may wirelessly communicate with one another. Wire 121 may also be omitted when the control unit 120 houses a magnetic field generator and the collar contains magneto-rheologic fluid, as discussed in more detail below with respect to FIG. 7.

In practice, as shown more clearly in FIG. 4, the collar 110 is placed to encircle the anatomical conduit U. The implantable control unit 120, or battery, is placed within the patient's body (portions shown schematically in dashed lines). In the case of a collar 110 filled with an electro-rheologic fluid, an electric current provided from the implantable control unit 120, or battery, and through the wire 121 and leads 121a, 121b to the collar 110 that generates an electrical potential difference. The electrical potential difference changes the electro-rheological fluid in the collar 110. For example, the presence of the electrical potential difference solidifies the electro-rheologic fluid in the collar 110, whereas the absence of the electric potential difference liquefies the fluid in the collar.

The sensor 130 is located anatomically upstream of the collar 110 within the anatomical conduit or organ to be emptied through the anatomical conduit that the collar 110 is placed upon. The sensor 130 collects bodily fluid pressure data within the anatomical conduit or organ to be emptied through the anatomical conduit. Where the sensor 130 and implantable control unit 120, or battery, are wireless, the wire 122 shown in FIG. 4 is omitted, as should be readily appreciated by the artisan.

Referring still to FIG. 4, the implantable control unit 120 may be provided with "ON" and "OFF" modes. When in the "ON" mode, for example, the implantable control unit 120 generates an electrical potential difference, for example. When in the "OFF" mode, the implantable control unit 120 does not generate an electrical potential difference. When the implantable control unit 120, for example, is in the "ON" mode, the electrical potential difference generated by the implantable control unit 120 solidifies the variable viscosity fluid within the collar 110. The solidified variable viscosity fluid in the collar 110 restricts the anatomical conduit from expanding, which restricts fluid from passing through the anatomical conduit. When the implantable control unit 120 is in the "OFF" mode the electrical potential difference is terminated or absent. In the absence of the electrical potential difference, the variable viscosity fluid in the collar 110 liquefies, rendering the collar 110 pliable, which permits the anatomical conduit to expand. The expanded anatomical conduit permits fluid to flow through the anatomical conduit when intended.

Switching the implantable control unit 120 between the "ON" and "OFF" modes can occur automatically based on sensed pressure data received by the sensor 130. For example, when sensed pressure meets or exceeds a pre-programmed pressure threshold level, the mode of the implantable control unit may be switched from "ON" to "OFF". Alternatively, when the patient manually operates an external control unit 140 (FIG. 5) provided with overriding Active input state having "Collar ON" and "Collar OFF" modes, then the implantable control unit mode may be switched accordingly to comply with the selected "Collar ON" or "Collar OFF" mode of the external control unit 140.

The implantable control unit 120 is pre-programmed with the pre-set pressure threshold level. Such pre-set pressure level varies according to organ or anatomical conduit capacities and according to patient preferences, as the artisan should appreciate. Generally, the lower the pre-set pressure threshold level of the sensor 130, the more often the implantable control unit 120 will generate an electrical potential difference.

The implantable control unit 120 can also be automatically switched from an "ON" mode to an "OFF" mode based on a pre-programmed upper pressure limit. The pre-programming aspects of the invention will be described in further detail below.

Alternatively, the battery, where provided as the implantable control unit 120, may provide the electrical potential difference to the leads 121a, 121b whenever the battery is energized. The battery may be normally de-energized, or "OFF", such that the electrical potential difference is normally absent. The battery may be automatically de-energized according to sensed pressure data received from the sensor 130, or according to patient operation of the external control unit 140 (FIG. 6). When energized, the battery would generate an electrical potential difference that solidifies the variable viscosity fluid within the collar.

As described above, with respect to the implantable control unit 120 shown in FIG. 4, when the battery is energized and an electrical potential difference is generated, fluid flow through the anatomical conduit is restricted due to the solidified variable viscosity fluid within the collar 110, whereas when the battery is not energized and the electrical potential difference is not generated, fluid flow through the anatomical conduit is permitted due to the pliable collar 110 and resulting expandable anatomical conduit.

As also with the implantable control unit 120 described above, once the sensed pressure data exceeds a pre-set threshold level, the sensor 130 communicates the excess level to the battery, causing the battery to de-energize and terminate production of the electrical potential difference. The variable viscosity fluid in the collar 110 is liquefied as a result. As a further result of the liquefied state of the variable viscosity fluid, the collar 110 becomes pliable permitting expansion of the anatomical conduit surrounded by the collar 110, and fluid flow therethrough the anatomical conduit.

FIG. 5 illustrates an external control unit 140 that is operated at will by the patient. The external control unit 140 is provided with an Active input state and an Inactive state. In the Inactive state, the external control unit 140 does not influence the operation of the implanted control unit 120. When in the Active state, the external control unit 140 responds to the "Collar ON" or "Collar OFF" mode selected an input to the external control unit by the patient. The "Collar ON" or "Collar OFF" mode is thus communicated wirelessly to the implantable control unit 120, or battery, by the patient. The external control unit 140 includes a "Collar ON" button 141, a "Collar OFF" button 142, and a display screen 143. When the external control unit 140 is in the Active state and in the "Collar ON" mode, the external control unit 140 overrides the sensor 130 and the implantable control unit 120 "OFF" mode and causes the implantable control unit 120, or battery, to generate an electrical potential difference between the leads 121a, 121b that is communicated to the collar 110 to solidify the electro-rheologic fluid in the collar regardless of the sensed pressure data received by the sensor 130. When the external control unit 140 is in the Active state and in the "Collar OFF" mode, the external control unit 140 overrides the sensor 130 and the implantable control unit "ON" mode and terminates the electrical potential difference from the implantable control unit, thereby liquefying the electro-rheological fluid within the collar. The patient can easily identify what state and mode the external control unit 140 is in by glancing at the display screen 143.

FIGS. 6A-6C illustrate exemplary stages of deployment of an anatomically placed artificial sphincter system according to the invention. More specifically, FIGS. 6A-6C show various states of deployment of the variable viscosity fluid-filled collar 110 around an anatomical conduit, wherein the state of deployment of the collar 110 corresponds to the state of the variable viscosity fluid within the collar 110 and the implanted control unit 120 has been pre-programmed to switch from an "OFF" mode to an "ON" mode when a pre-set pressure threshold limit is met or exceeded, and to switch from the "ON" mode to an "OFF" mode when a pre-set upper pressure limit in one of the bladder B, or anatomical conduit U, has been reached.

For example, FIG. 6A shows the collar 110 in a soft, pliable state overlying the natural sphincter muscle (not shown) and surrounding the anatomical conduit U. As shown in FIG. 6A, the organ, for example bladder B, to be emptied through the anatomical conduit U shown in FIG. 6A is experiencing a pressure level below the pre-programmed threshold level. The natural sphincter muscle is thus adequate to restrict fluid flow through the anatomical conduit U in this case. Because the implanted control unit 120 is in a normally "OFF" mode, the patient need not override the implanted control unit 120 by operating the external control unit 140 to an "OFF" mode. The external control unit 140 may be in the Inactive state therefore. The variable viscosity fluid within the collar 110 is thus liquefied in FIG. 6A

As shown in FIG. 6B, once the pressure in the bladder B or urethra U meets or exceeds the pre-set pressure threshold limit, the implanted control unit 120 switches from the normally "OFF" mode of FIG. 6A, to the "ON" mode. In the "ON" mode, an electrical potential difference is generated by the implanted control unit 120 and applied to the collar 110 via the leads 121a, 121b. The electrical potential difference causes the variable viscosity fluid within the collar 100 to solidify and restrict fluid flow through the urethra U, as shown in FIG. 6B.

Referring now to FIG. 6C, an upper pressure limit is also pre-programmed into the implantable control unit 120 according to the patient's individual bladder B or urethra U capacities, for example. The upper pressure limit is programmed into the implanted control unit 120 in conventional manner using the programming means, such as the computer and software, discussed above with respect to the pre-set pressure threshold limits. As shown in FIG. 6C, the implanted control unit 120 switches from the "ON" mode to the "OFF" mode when the upper pressure limit in the bladder B or urethra U is approached.

The upper pressure limit within the bladder B or conduit U may be approached as a result of the natural accumulation of bodily fluids therein, and/or by the patient's exercising of abdominal and/or pelvic muscles. Ideally, the implanted control unit 120 is pre-programmed to switch from the "ON" mode to the "OFF" mode only after the pre-programmed upper pressure limit has been sustained for a pre-determined time limit, for example 3 seconds. In this manner, the bladder B, or urethra U, may be emptied without risk of rupture or undue discomfort to the patient even if the external control unit 140 was lost, inoperable, or otherwise unavailable. The predetermined time limit should be long enough to avoid accidental switching of the implanted control unit to "OFF" by a brief application of abdominal muscles, which could be caused by sudden and brief peaks in bladder pressure, e.g., during sneezing.

When the electro-rheologic fluid in the collar 110 is liquefied and the collar is rendered pliable, the electric potential difference should remain absent for a period of time, for example, one minute in order to permit the organ or anatomical conduit to empty sufficiently. Ideally, the organ or conduit would empty sufficiently to effect a pressure drop in the organ or anatomical conduit below the upper threshold. In this manner, the implanted control unit 120, or battery, will not switch to its "ON" mode too soon, i.e., in the middle of the act of emptying the organ or anatomical conduit, such as one's bladder.

Of course, the patient may also choose at any time to operate the external control unit 140 to the Active state and the "Collar OFF" mode thereby overriding the "ON" mode of the implantable control unit 120. With the external control unit in the Active state and the "Collar OFF" mode, the implantable control unit 120 does not generate an electrical potential difference, and the variable viscosity fluid in the collar 110 is liquefied. The override of the implanted control unit 120 by operation of the external control unit 140 would expire after a designated time period. Once the override has expired, the implanted control unit 120 would resume its normally "OFF" state until either the pre-set pressure threshold limit is exceeded or the external control unit 140 is switched to the Active state and the "Collar ON" mode to override the normally "OFF" state of the implanted control unit.

In FIG. 6B, after the pre-set pressure threshold limit has been exceeded or the external control unit 140 has been operated to override the normally "OFF" state of the implantable control unit, the implanted control unit 120 is switched to the "ON" mode. The implanted control unit 120 thus generates an electrical potential difference that is communicated to the collar via the leads 121a, 121b. As a result, the variable viscosity fluid in the collar 110 is solidified, which restricts the anatomical conduit U from expanding, which in turn restricts the unintentional flow of fluids from the organ B through the anatomical conduit U.

As shown in FIG. 6C, after either the upper pressure limit has been reached or the external control unit 140 has been operated in the Active state and the "Collar OFF" mode to override the "ON" mode of the implanted control unit 120, the implanted control unit 120 is switched to the "OFF" mode. Switching the implanted control unit 120 to the "OFF" mode terminates the electrical potential difference, which liquefies the variable viscosity fluid and renders the collar 110 pliable. Expansion of the anatomical conduit U and elimination of the fluid from the organ B through the anatomical conduit U as shown by arrow a is thus permitted. Of course, the implanted control unit 120 automatically switches to the "OFF" mode whenever the pre-programmed upper pressure limit is approached.

The pre-set pressure threshold limit for each patient is set slightly below that limit at which the natural sphincter becomes insufficient. Such pre-set pressure threshold limits are therefore pre-programmed into the implantable control unit 120 according to individual patient needs. The pre-set pressure threshold limits are input to the implanted control unit 120 using programming means such as, for example, software and a computer that communicates the various settings to the implanted control unit 120 in conventional manner. The pre-set pressure threshold levels can be re-programmed into the implantable control unit 120 to accommodate changing needs or conditions of the patient.

The upper pressure limit is similarly pre-programmed into the implanted control unit 120. Likewise, the pre-determined time limit that the upper pressure limit must be sustained for before switching the implantable control unit 120 from the "ON" mode to the "OFF" mode is also pre-programmed into the implanted control unit. Once pressure in the bladder B or conduit U has dropped below the pre-set threshold level, the implanted control unit 120 resumes its normally "OFF" state until the pre-set threshold level is met or exceeded, or until the external control unit 140 is operated to switch the implanted control unit from the "OFF" mode to the "ON" mode.

Although the embodiments described thus far describe generally an artificial sphincter system having a collar 110 filled with a variable viscosity fluid that changes viscosity states according to the presence or absence of an electrical potential difference, as where the variable viscosity fluid is an electro-rheologic fluid, the variable viscosity fluid could instead be a magneto-rheologic fluid contained within the collar 110. In this case, the variable viscosity fluid would change states according to the presence or absence of conditions such as a magnetic field rather than according to the presence or absence of an electrical potential difference.

Figure 7:
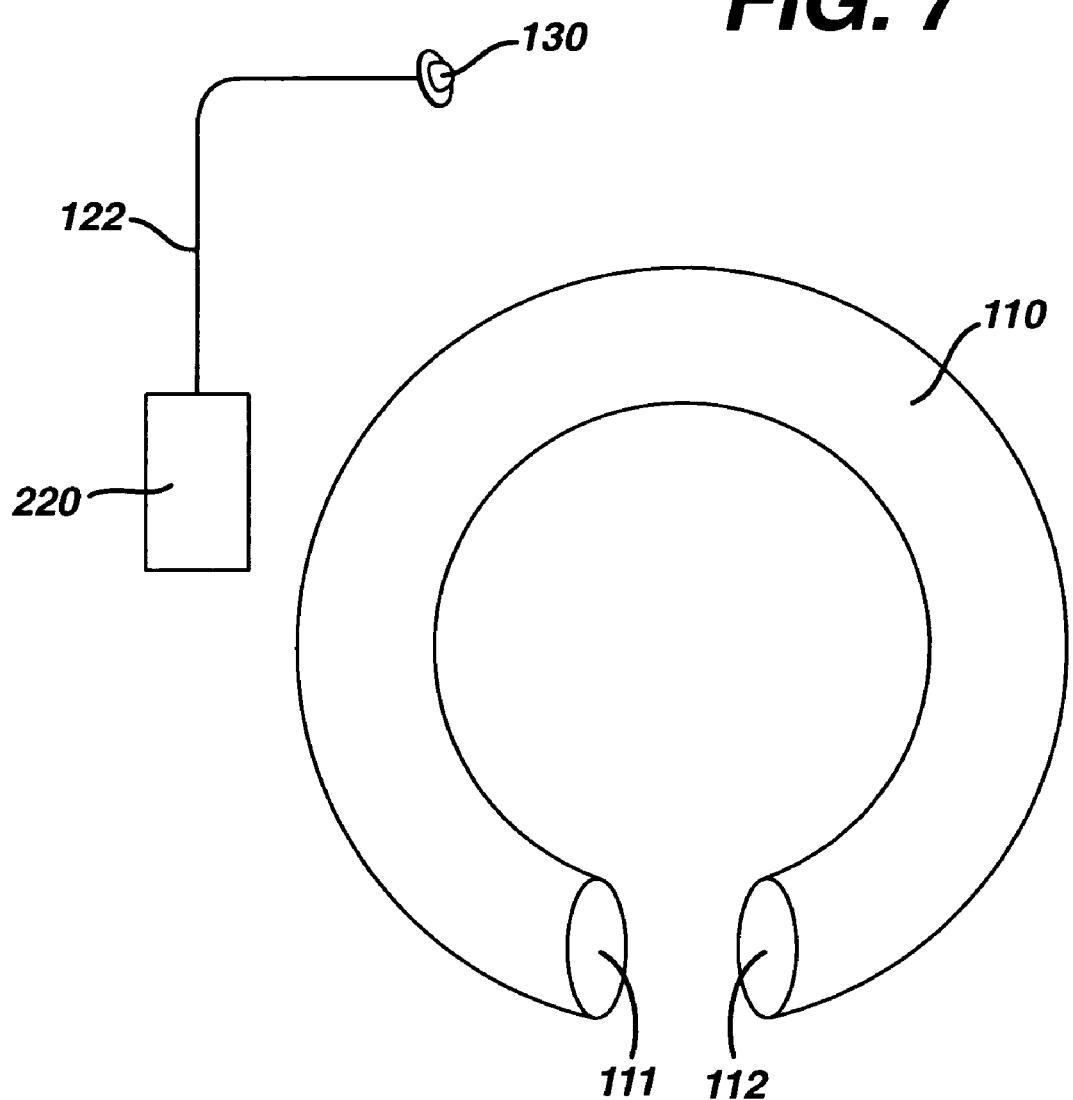
FIG. 7 illustrates an embodiment of the artificial sphincter system having a magneto-rheologic fluid contained within the collar according to the invention.

As shown in FIG. 7, wherein like numerals represent like components, the artificial sphincter system comprised of a collar 110 filled with a magneto-rheologic fluid as the variable viscosity fluid would comprise substantially the same components and would operate generally as described above with reference to the artificial sphincter system shown in FIGS. 3-6, the notable differences being described in more detail herein with respect to FIG. 7. For example, rather than an implanted control unit 120, or battery, to generate an electrical potential difference as in earlier embodiments, FIG. 7 shows a control unit comprising a magnetic field generator 220 that would generate a magnetic field according to this embodiment of the invention.

The artisan will appreciate that the various components comprising the artificial sphincter system having magneto-rheologic fluid within the collar 110 as shown in FIG. 7 may be wired to one another, or may wirelessly communicate with one another, generally similarly to as described above with respect to earlier embodiments of the invention presented herein. However, where the collar is filled with a magneto-rheologic fluid the wire 121 connecting the collar 120 to the implanted control unit 120 of earlier embodiments may be omitted in this embodiment as such a wire is not necessary to disseminate a magnetic field from the magnetic field generator 220 to the collar. Further, the control unit comprised of the magnetic field generator 220 need not be implanted within the body. Rather, an external magnetic field generator (not shown) may instead be used where the collar 110 is filled with a magneto-rheologic fluid. The artisan should readily appreciate that the where the magnetic field generator 220 is external, wire 122 is also omitted and the sensor 130 wirelessly communicates with the external magnetic field generator.

Where provided, the implanted magnetic field generator 220 would be anatomically placed similarly to the implanted control unit 120, or battery, of earlier described embodiments. Moreover, the implanted magnetic field generator 220, operating in a normally "OFF" mode would not generate a magnetic field. The absence of the magnetic field would liquefy the magneto-rheologic fluid within the collar 110 and permit expansion of the anatomical conduit U, which would in turn permit fluid flow therethrough the anatomical conduit U. Conversely, the magnetic field would be generated when the implanted magnetic field generator 220 is in the "ON" mode. The presence of the magnetic field would solidify the fluid within the collar 110, thus restricting the anatomical conduit with the solidified collar and restricting fluid from flowing through the anatomical conduit. Switching the implantable magnetic field generator 220, or other implantable magnetic source, between the "ON" and "OFF" modes can occur automatically according to sensed-pressure data received by the sensor 130, or can occur manually according to operation of the external control unit 140 by the patient as with the earlier described embodiments.

FIG. 8 illustrates another embodiment of a collar 1110 according to the invention, wherein like numerals refer to like features. The collar 1110 shown in FIG. 8 is generally the same as the collar 110 described above with respect to FIGS. 1-7, for example, but in addition comprises a plurality of compartments 1111 throughout the collar 1110. The compartments 1111 are created by internal walls 1112 connecting the outer diameter Do and the inner diameter D of the collar 1110. Each of the compartments 1111 contains variable viscosity fluid as described above.

Further, the variable viscosity fluid in each of the compartments 1111 can be independently controlled such that all of the compartments liquefy or solidify at the same time, or such that alternating ones of the compartments solidify and the remaining compartments are liquefied. Wires 1121 and leads 1121a, 1121b, for example, connect the compartments 1111 to the implanted control unit 120 to independent change the state of compartments 1111 of the collar where electro-rheologic fluid is contained within the collar 1110.

Where the compartments 1111 are filled with a magneto-rheologic fluid, the compartments 1111 are each filled with a different magneto-rheologic fluid. In this manner, each fluid reacts differently according to the same magnetic field generated by the magnetic field generator 220, which may be implanted or external to the body, as described earlier. The leads 1121a, 1121b are omitted where a magneto-rheologic fluid fills the collar 1110.

Figure 9:
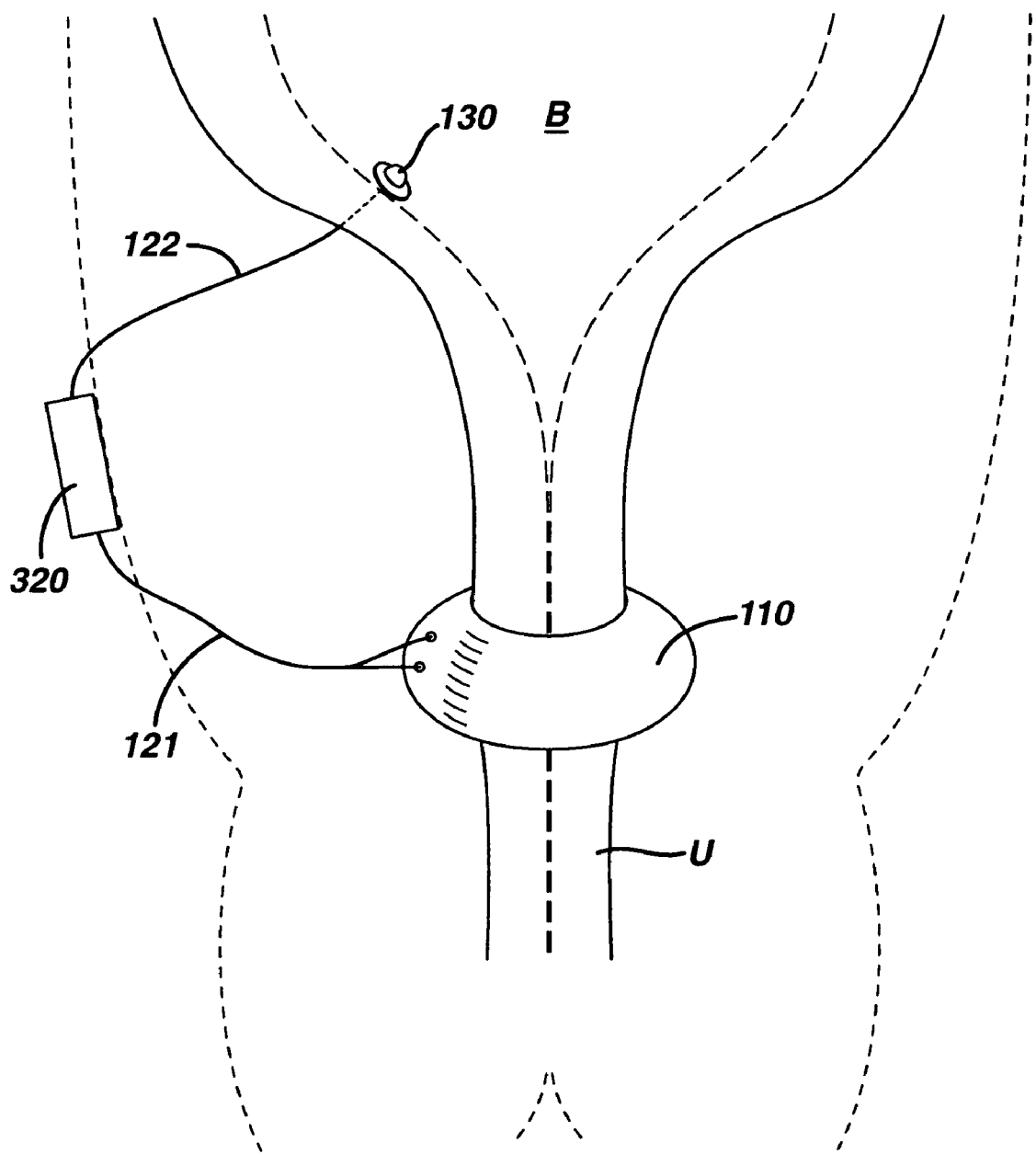
FIG. 9 illustrates another embodiment of a collar containing electro-rheological fluid without an implantable control unit according to the invention.

FIG. 9 illustrates yet another embodiment of the systems and methods of the invention with respect to a collar filled with an electro-rheologic fluid, wherein like numerals refer to like features where appropriate. The embodiment of FIG. 9 is generally the same as the embodiment of FIG. 4 except that the implantable control unit 120 is omitted in FIG. 9. Because the implanted control unit 120 is omitted, the wire 121 extends from the collar 110, where leads 121a, 121b connect the wire 121 to the collar 110, to a location external of the patient's body, as shown in FIG. 9. The wire 121 connects to another control unit 320 external of the body. As in earlier described embodiments, the sensor 130 is placed in the organ or anatomical conduit and communicates sensed data to the control unit 320 to generate an electrical potential difference across the leads 121a, 121b on the collar. The sensor 130 may be a wireless sensor as described above with respect to FIG. 4, or may be hard-wired using wire 122 in conventional manner as discussed above. The presence or absence of an electrical potential difference determines the state of the electro-rheologic fluid within the collar as before, wherein the presence of an electrical potential difference solidifies the fluid in the collar, and the absence of he electrical potential difference liquefies the fluid in the collar. The artisan should readily appreciate that the control unit 320 may be adhered to the skin of the patient, may be fitted to the patient in a belt, or may be otherwise fitted externally to the patient in an other equally conventional manner. The external nature of the control unit 320 may render the unit easier to service than implantable counterparts.

The various exemplary embodiments of the invention as described hereinabove do not limit different embodiments of the present invention. The material described herein is not limited to the materials, designs, or shapes referenced herein for illustrative purposes only, and may comprise various other materials, designs or shapes suitable for the systems and procedures described herein as should be appreciated by one of ordinary skill in the art.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. An artificial sphincter system comprising:
   a collar adapted to surround a portion of an anatomical conduit, the collar comprising a flexible, biocompatible material having a substantially circular configuration with closed ends connectable to one another;
   a variable viscosity fluid contained within the collar, the variable viscosity fluid having at least a liquefied state and a solidified state, the collar includes a plurality of compartments formed from inner walls, each compartment comprising independently controlled variable viscosity fluids;
   a sensor that receives pressure data from the anatomical conduit or organ to be emptied through the anatomical conduit;
   a first control unit having an "ON" mode that creates conditions that change the variable viscosity fluid within the collar from the liquefied state to the solidified state, and an "OFF" mode that changes the variable viscosity fluid from the solidified state to the liquefied state, wherein the collar having the variable viscosity fluid in a solidified state restricts fluid flow through the anatomical conduit, and the collar having the variable viscosity fluid in a liquefied state permits fluid flow through the anatomical conduit, the first control unit being configured to apply at least one of an electric potential or magnetic field to the variable viscosity fluid contained within the collar, the first control unit being implantable within the patent; and
   a second control unit operable by a patient, the second control unit having only an active input state and an inactive input state, wherein the active state of the second control unit overrides the current mode of the first control unit, the second control unit includes a display screen identifying whether the second control unit is active or inactive.

2. The artificial sphincter system of claim 1, wherein the first control unit mode is determined according to the pressure data received by the sensor and communicated to the first control unit or according to operation of the external control unit.

3. The artificial sphincter system of claim 2, wherein the first control unit further comprises a pre-set pressure threshold level that changes the first control unit to the "OFF" mode to liquefy the variable viscosity fluid when the pre-set threshold level is met or exceeded.

4. The artificial sphincter system of claim 3, wherein the first control unit further comprises a pre-set upper pressure level and a designated time factor that changes the first control unit to the "OFF" mode to liquefy the variable viscosity fluid when the pre-set upper pressure level is sustained for the designated time factor.

5. The artificial sphincter system of claim 4, wherein the variable viscosity fluid is an electro-rheologic fluid, changeable between the liquefied state and the solidified state based on the presence or absence of the field.

6. The artificial sphincter system of claim 5, wherein the conditions created by the first control unit are an electrical potential difference communicated to solidify the fluid within the collar.

7. The artificial sphincter system of claim 6, further comprising a wire extending from the first control unit to the collar, the wire having at least two leads placed on the collar to communicate the electrical potential difference to the fluid within the collar.

8. The artificial sphincter system of claim 6, wherein the first control unit is a battery.

9. The artificial sphincter system of claim 6, wherein the first control unit is external of the body of the patient.

10. The artificial sphincter of claim 2, wherein the collar is pliable when the variable viscosity fluid is in the liquefied state permitting expansion of the anatomical conduit, and the collar is rigid when the variable viscosity fluid is in the solidified state restricting expansion of the anatomical conduit.

11. The artificial sphincter system of claim 10, wherein the variable viscosity fluid is a magneto-rheologic fluid, changeable between the liquefied state and the solidified state based on the presence or absence of the created conditions.

12. The artificial sphincter system of claim 11, wherein a magnetic field is the conditions created by the first control unit to solidify the fluids within the collar.

13. The artificial sphincter system of claim 1, further comprising securing devices for securing the collar to the portion of the anatomical conduit.

14. The artificial sphincter system of claim 13, wherein the securing devices are any of snaps, buttons, sutures, and clamps.

15. The artificial sphincter system of claim 1, wherein the sensor, first control unit, collar and external control unit wirelessly communicate with one or more of each other.

16. The artificial sphincter system of claim 1, wherein the sensor is wired to the first control unit by a first wire and the first control unit is wired to the collar by a second wire, and the external control unit wirelessly communicates with the first control unit.

* * * * *